United States Patent [19]

Thomas, II et al.

[11] 4,405,354

[45] Sep. 20, 1983

[54] ELIMINATION OF ODORS FROM WASTE MATERIAL

[75] Inventors: Johnny M. Thomas, II, Fort Collins; Richard P. Mommer, Loveland, both of Colo.

[73] Assignee: Uniscope, Inc., Johnstown, Colo.

[21] Appl. No.: 136,553

[22] Filed: Apr. 2, 1980

[51] Int. Cl.³ .......................... A01K 1/015; C05F 3/00
[52] U.S. Cl. .......................................... 71/21; 71/903; 71/904; 71/64.11; 71/64.13; 422/17; 119/1
[58] Field of Search ...................... 71/3, 23, 25, 11, 27, 71/32, 64 G, 15, 21, 903, 904, 64.11, 64.13; 422/17; 119/1

[56] References Cited

U.S. PATENT DOCUMENTS

| | | | |
|---|---|---|---|
| 2,218,695 | 10/1940 | Leatherman | 71/8 |
| 2,714,553 | 8/1955 | Bibb et al. | 71/904 |
| 3,369,884 | 2/1968 | Barron | 71/64.11 X |
| 3,580,715 | 5/1971 | Dilday | 71/64.13 X |
| 4,263,873 | 4/1981 | Christianson | 119/1 |

FOREIGN PATENT DOCUMENTS

| | | | |
|---|---|---|---|
| 2401120 | 4/1979 | France | 71/64 C |
| 50-13539 | 2/1975 | Japan | 422/5 |
| 51-18669 | 2/1976 | Japan | 71/21 |

*Primary Examiner*—Ferris H. Lander
*Attorney, Agent, or Firm*—Lackenbach, Siegel, Marzullo, Presta & Aronson

[57] ABSTRACT

A method and composition for the elimination and control of ammonia odor from organic waste materials by contacting the waste material with a composition containing a deodorizing agent which produces a non-odorous ammonia salt, thereby eliminating gaseous ammonia from escaping into the air. The present invention also eliminates additional odors resulting from putrefaction due to ammonia fixing bacteria.

24 Claims, No Drawings

ELIMINATION OF ODORS FROM WASTE MATERIAL

BACKGROUND OF THE INVENTION

1. Field of the Invention

This invention relates to the elimination of odors from waste material, and more specifically to the elimination and control of ammoniacal odors from animal and human excreta. The pungent and unpleasant odor of ammonia emanating from organic waste products subject to chemical or microbial degradation is a public nuisance as well as a health hazard, particularly in situations where waste products are left to accumulate over periods of time, such as days, weeks and even months.

Ammonia is formed as the end product in the degradation of urea by the enzyme urease, and the enzyme degradation of uric acid to form urea, and then ammonia. Urea and uric acid are products of protein catabolism. In certain specific environments such as poultry houses, the concentration of ammonia in the air can become so high, that it can cause ammonia blindness in the poultry, thereby causing production losses through the reduced consumption of feed.

Ammonia fumes in pig farrowing houses can lead to respiratory illness, such as pneumonia, in piglets. The odor of ammonia is also a problem in privies, zoological gardens, and sewage treatment facilities. The keeping of domesticated pets such as cats, dogs, hamsters, guinea pigs, birds, and the like, where excreta can accumulate in cages, pens or other in-house facilities also gives rise to objectionable ammonia odors.

Many efforts have been made to ameliorate the problem of odor emanating from waste materials by the use of certain substances to cover up or "mask" the odor. However, this approach does not remove or eliminate odor, especially the ammonia odor. Other methods have dealt with controlling different odors associated with the decay of fecal and other waste materials, such as mercaptans, dialkylsulfides, hydrogen sulfide and skatole. These methods have not been successful in controlling or eliminating ammonia odors emanating from the waste materials.

2. Description of the Prior Art

A number of prior art approaches have used various chemical compositions to deal with the odor problems of various organic waste materials. U.S. Pat. No. 3,944,908 to Postrihac discloses a biological fertilizer produced from the treatment of sewage sedimentation sludge with a sulfite waste liquor at a pH of no more than 6, followed by mixing the treated sludge with pulverized vegetable matter. U.S. Pat. No. 4,108,771 to Weiss reduces odors from waste material by contacting them with an aqueous acid solution containing an oxidizing agent, for example, water soluble persulfates, nitrates, chlorates and permanganates of ammonia and alkali metals, and a precipitating agent which is a water soluble ferrous or ferric compound. Inorganic acids, such as sulfuric acid are disclosed as most efficient, although acid salts may also be employed, such as peroxydisulates (persulfates), hydrogen sulfates, ferric chloride and the like. The amount of acid material employed in the mixture is designed to provide a pH of up to about 6.5.

U.S. Pat. No. 124,041 to Dotch discloses deodorizing night soil with sulfuric and hydrochloric acid. U.S. Pat. No. 125,886 to Dotch discloses a method for deodorizing night soil and converting it into fertilizer by mixing it with sulfuric acid, hydrochloric acid, and potassium nitrate. U.S. Pat. No. 705,462 to Smith discloses a method for making fertilizer from excreta by adding it to phenol, calcium carbonate and alumina silicate.

U.S. Pat. No. 3,978,208 to Okada discloses a composition for deodorizing excrement, which contains derivatives of hydroxamic acid as the active ingredient. U.S. Pat. No. 3,989,498 to Cox discloses a deodorant composition for sewage sludge which is then spread as a slurry on land for restoring fertility. The deodorant composition contains glacial acetic acid and amyl alcohol. It can also include sulfuric acid, 2-3-butanedione, benzaldehyde, hydrochloric acid and copper sulfate. U.S. Pat. No. 4,127,383 to Johnstown et al discloses a composition consisting of a salt of lignosulfonic acid and a foaming surfactant system for use in treating nitrogenous wastes. The composition, applied to proteinaceous materials stabilizes the amines and ammonia contained therein. A foam stabilizer such as callulose gum can be an additional component.

A number of prior art approaches have also addressed themselves to the problem of deodorizing animal wastes. U.S. Pat. No. 3,983,842 to Marion et al discloses a pelleted animal litter containing as its major ingredient, ground peanut hulls with sodium bicarbonate as the odor suppressor. Other odor suppressors include calcium carbonate, trisodium phosphate and sodium carbonate. Filler materials include grass. U.S. Pat. No. 3,765,371 to Fisher prefers synthetic materials, such as high surface area foamed plastics, including polystyrene, polyurethane, phenolic resins, polyvinyl chloride, cellulose acetate, etc., rather than clays, bentonite, and alfalfa, as filler.

U.S. Pat. No. 3,735,734 to Pierce et al discloses an admixture of an absorbent such as clay or diatomaceous earth, and a deodorant, such as chlorophyl, sodium or potassium dihydrogen phosphate, or potassium acid phthalate. U.S. Pat. No. 3,675,625 to Miller et al discloses an absorbent of clay, vermiculite, or earthen material, and an odor control material such as menthol, camphor or other phenolic materials. U.S. Pat. No. 3,636,927 to Baum discloses camphane derivatives as odor inhibiting substances, along with a number of conventional solid carriers.

U.S. Pat. No. 3,352,792 to Clark et al uses a deodorant composition comprising a borate, such as borax and magnesium carbonate. U.S. Pat. No. 3,286,691 to McFadden utlilizes dehydrated grasses, preferably alfalfa and includes absorbing aids such as bentonite and trimethylquinoline. U.S. Pat. No. 3,029,783 to Sawyer et al discloses an aluminum salt and sorptive carrier.

Although several approaches have addressed themselves to the elimination and control of odors from waste materials, none of them effectively deal with ammoniacal odors. Bactericides such as 6-ethoxy-1,2-dihydro-2,2,4-trimethylquinoline have also been used, but they are not effective. The state of the art approaches generally seek to deal with all odors emanating from animal and human waste materials, and, in so doing, do not successfully deal with the problem of controlling and eliminating ammonia odor.

SUMMARY OF THE INVENTION

In accordance with the present invention, the problem of ammonia odor emanating from waste materials is eliminated and controlled by contacting the waste material with a composition containing a deodorizing agent which produces a non-odorous ammonium salt, thereby eliminating gaseous ammonia from evolving into the air. The present invention also eliminates additional odors resulting from putrefaction due to ammonia fixing bacteria.

DETAILED DESCRIPTION OF THE INVENTION

The odor control composition of the present invention utilizes monobasic salts of dibasic acids and mono- or dibasic salts of tribasic acids, etc and mono-, or di-, or tri- etc basic acids, as the ammonia control agent. These include the oxo acids of sulfur and phosphorus, alkali metal monobasic salts of the oxo acids of sulfur, dibasic salts of the oxo acids of phosphorus, and alkaline earth dibasic salts of the oxo acids of sulfur and phosphorus.

It has been found that for the aforesaid substances to be operable as ammonia control agents the value of their dissociation constant, $pK_a$, should be less than the dissociation constant of aqueous ammonia. The dissociation constant, also referred to as the equilibrium constant is the product of the concentrations (or activities) of the substances produced at equilibrium in a chemical reaction divided by the product of concentrations of the reacting substances, each concentration raised to that power which is the coefficient of the substance in the chemical equation.

Approximate equilibrium constants may be derived employing molalities, mole fractions, partial pressures or the equivalent quantities that are usually measured. However, the activities or fugacities must be employed to derive exact constants.

The *Handbook of Chemistry and Physics*, (59th edition, CRC Press 1978) at page D-203 lists dissociation constants for aqueous ammonia, tabulated as follows:

| DISSOCIATION CONSTANTS ($K_b$) OF AQUEOUS AMMONIA FROM 0 to 50° C. | | |
|---|---|---|
| Temperature °C. | $pK_b$ | $K_b$ |
| 0 | 4.862 | $1.374 \times 10^{-5}$ |
| 5 | 4.830 | $1.479 \times 10^{-5}$ |
| 10 | 4.804 | $1.570 \times 10^{-5}$ |
| 15 | 4.782 | $1.652 \times 10^{-5}$ |
| 20 | 4.767 | $1.710 \times 10^{-5}$ |
| 25 | 4.751 | $1.774 \times 10^{-5}$ |
| 30 | 4.740 | $1.820 \times 10^{-5}$ |
| 35 | 4.733 | $1.849 \times 10^{-5}$ |
| 40 | 4.730 | $1.862 \times 10^{-5}$ |
| 45 | 4.726 | $1.879 \times 10^{-5}$ |
| 50 | 4.723 | $1.892 \times 10^{-5}$ |

The dissociation constant, $pK_a = 14 - pK_b$. The dissociation constant, $pK_a$, for aqueous ammonia will vary from about 9.1 to about 9.4.

For those applications where the elimination and control of ammonia from waste materials occurs over a relatively extensive area, such as in broiler houses or farrowing pens, the odor control composition is preferably applied in the form of a liquid or spray utilizing the oxo acids of sulfur or phosphorus, such as orthophosphoric acid, pyrophosphoric acid, hypophosphoric acid, phosphorous acid, pyrophosphorus acid, hypophosphorous acid, sulfuric acid, pyrosulfuric acid, dithionic acid, sulfurous acid, pyrosulfurous acid, sulfoxylic acid, and the like, as well as organic acids including formic acid, acetic acid, propionic acid, lactic acid, and the like, can be used as well. The amount of odor control agent should be sufficient to effectively eliminate or control the ammonia odor, and at the same time, not be toxic or harmful to the environment or animal occupants in the immediate vicinity.

On a smaller scale, the ammonia control composition can preferably be used in the form of a pellet or as a finely divided premixed litterbox additive for domesticated animals and pets. The active ammonia control component in the form of a pellet can preferably be an alkali metal monobasic salt of the oxo acid of sulfur and the dibasic salts of the oxo acids of phosphorus, alkaline earth dibasic salts of oxo acids of sulfur and phosphorus, and certain solid organic acids, such as benzoic, ethylenediaminetetraacetic acid (EDTA), maleic acid, citric acid, malonic acid, succinic acid, malic acid, adipic acid, fumaric acid, and the like.

Alkali metals include lithium, sodium potassium, rubidium and cesium. Alkaline earth metal includes beryllium, magnesium, calcium, strontium and barium.

Among the alkali metal and alkaline earth metal salts, sodium and calcium salts are most preferable due to their high efficiency, low toxicity, and economic availability. Sodium bisulfate is particularly preferred.

The following tables outline specific examples of preferred ammonia controlling compounds, whereas Table II exemplifies other compounds which do not work. The distinction between the viable ammonia control compounds and those compounds which do not work is their respective dissociation constants, $pK_a$. The listed compounds which control ammonia have $pK_a$'s which are lower than that of aqueous ammonia, whereas those which do not work have dissociation constants which exceed the $pK_a$ of aqueous ammonia.

TABLE I

| AMMONIA CONTROL COMPOUNDS | | |
|---|---|---|
| Inorganic Acids | Alkali Metal Salts (M) | Alkaline Earth Salts (Me) |
| $H_3PO_4$ | $MH_2PO_4$ | $Me(H_2PO_4)_2$ |
| $H_4P_2O_7$ | $M_2H_2P_2O_7$, $M_3HP_2O_7$ | $MeH_2P_2O_7$, $Me_3(HP_2O_7)_2$ |
| $H_4P_2O_6$ | $M_2H_2P_2O_6$, $M_3HP_2O_6$ | $MeH_2P_2O_6$, $Me_3(HP_2O_6)_2$ |
| $H_3PO_3$ | $MH_2PO_3$ | $Me(H_2PO_3)_2$ |
| $H_4P_2O_5$ | $M_2H_2P_2O_5$, $M_3HP_2O_5$ | $MeH_2P_2O_5$, $Me_3(HP_2O_5)_2$ |
| $H_3PO_2$ | $MHSO_4$ | $Me(HSO_4)_2$ |
| $H_2SO_4$ | $MHS_2O_7$ | $Me(HS_2O_7)_2$ |
| $H_2S_2O_7$ | $MHS_2O_6$ | $Me(HS_2O_6)_2$ |
| $H_2S_2O_6$ | $MHSO_3$ | $Me(HSO_3)_2$ |
| $H_2SO_3$ | $MHS_2O_5$ | $Me(HS_2O_5)_2$ |
| $H_2S_2O_5$ | $MHSO_2$ | $Me(HSO_2)_2$ |
| $H_2SO_2$ | | |

TABLE II

| COMPOUNDS WHICH DO NOT CONTROL AMMONIA | | |
|---|---|---|
| Acids | Alkali Metal Salts | Alkaline Earth Salts |
| $H_3BO_3$ | $M_2HPO_4$ | $MeHPO_4$ |
| HCl | $M_2HPO_3$ | $MeHPO_3$ |
| | $MH_2PO_2$ | $Me(H_2PO_2)_2$ |
| | $MHCO_3$ | |

When the ammonia control composition is applied to the waste material in the form of a liquid or spray, the concentration of the ammonia control component can vary from about 15 to 100% by weight, preferably from about 20 to 60% by weight of the total composition. The liquid or spray composition can also include water as a diluent, varying from about 40 to 85% by weight, preferably 50 to 80% by weight of the total composition. A viscosity additive or thickener, preferably a natural gum material can also be included to give body to the liquid or spray. These include pectin, xanthan gum, gum arabic, gum tragacanth, locust bean gum, tamarind, and guar gum. The natural gum thickener can vary from about 0.25-2% by weight, preferably 0.5 to 1% by weight of the total composition.

When the ammonia control agent is used in a pelleted composition, other components can include filler or roughage materials, such as straw, wood particles, alfalfa, ground peanut hulls, rice hulls, and the like. The filler component can vary from about 70-95% by weight of the total composition, but more preferably varies from about 85-92% by weight.

The ammonia control agent can be any of the compounds listed in Table I, preferably an alkali metal or alkaline earth salt, and most preferably sodium bisulfate. The ammonia control agent can vary from about 0.5 to 25% by weight, preferably from about 2 to 10% by weight of the total composition.

The pelleted composition can also include a binder material such as lignin sulfonate or other equivalent binder which does not react with the ammonia control agent in a manner which reduces its capacity to control the ammonia odor. The binder material can vary from about 0 to 5% by weight, preferably from about ½ to 2% by weight of the total composition.

The pelleted composition can also include materials to increase its absorbency, such as natural or synthetic gums including guar gum, pectin, xanthan, locust bean gum, tamarind polyacrylamide and the like. The absorbent component can vary from 0.05 to 10% by weight, preferably from 0.5 to 2.5% by weight of the total composition, and should not be adversely affected by low pH's in the range of about 2 to 3.

A pelleting additive can also be incorporated in the composition to assist the pelleting process and improve the binding properties of the finished pellet. A preferred pelleting additive is sold under the trademark "PEL-AID" (Uniscope, Inc., Johnstown, Colo.), and can be used in quantities up to 0.2% by weight, preferably from 0.05-0.1% by weight of the total composition.

In pelleting the ammonia control composition, the size of the pellet is not critical. Generally, it can vary from ⅛ inch to ½ inch in diameter, and ⅛ inch to 1 inch in length. A pellet 5/32 inch in diameter and about ¼ to ¾ inch in length is preferred, due to the fact that this die size is commonly available to form the pellet. Longer pellets tend to break easier and produce more dust and fine particles. Smaller diameter pellets slow down production. Large diameter pellets tend to crack open and produce dust and fine particles. The geometry of the pellet is a matter of choice, and it can be spherical, rectangular, elliptical, square or cylindrical in shape.

In another variation, the ammonia control composition can be used in a finely divided particulate form as a litterbox additive. The ammonia control component is preferably sodium bisulfate or sulfuric acid. When sulfuric acid is used as the ammonia control component, it is preferred that calcium sulfate be used as the filler material.

Other filler materials include wood particles, diatomaceous earth, clay, straw, ground peanut hulls, rice hulls, alfalfa and the like. The particle size of the litterbox additive is generally a matter of choice depending upon the particularities of its application and whether or not the animal will come into direct contact with the composition. Generally, a particle size of 60-80 mesh (0.250 to 0.177 millimeters) is adequate.

The proportions of ammonia control component to filler material also will vary, depending upon whether the animal will come into direct contract with the composition. When the animal is kept in a cage with openings in the floor which allow the excreta to fall through and collect on a pan or tray containing the ammonia control composition, the animal will not come into contact with the ammonia control composition.

Therefore the proportions of ammonia control component can be increased to the extent that it can be used without filler material in the case of sodium bisulfate. In general, the filler material can vary from 0 to 80% by weight, preferably 30 to 70% by weight of the total composition. The ammonia control component can vary from 20 to 100% by weight, preferably 30 to 70% by weight of the total composition.

With animal litter, particularly that of cats and dogs, the use of sodium bisulfate has been found to be particularly effective in dealing with and removing the ammonia odor. A concentration of sodium bisulfate of 10% by weight has eliminated the ammonia odor from the litter for up to eight weeks. As little as 0.5% exerts an effective control and up to 20% by weight is feasible.

The following examples set forth specific embodiments of the invention, and are not intended to limit the scope of the invention. All parts and percentages are by weight, unless otherwise noted.

EXAMPLE 1

5 grams of sodium bisulfate were placed into a beaker. 3.75 grams of ammonium hydroxide were added gradually on a dropwise basis. During the addition, the beaker was frequently checked to detect the odor of ammonia by smell. No ammonia could be detected until an amount of ammonium hydroxide exceeding 3.75 grams, the stoichiometrical amount, had been added, thereby resulting in an immediate, irritating, strong ammonia smell.

EXAMPLE 2

In a procedure identical to Example 1, several other chemicals were tested for their ability to neutralize ammonium hydroxide, thereby eliminating the odor of ammonia. In each instance 5 grams of the active chemical were used. In the data tabulated in Table III, each active chemical is listed next to the corresponding amount of ammonium hydroxide neutralized to the extent that no odor of ammonia was detected

TABLE III

| Active Chemical | $NH_4OH$ (grams neutralized) |
|---|---|
| $H_2SO_4$ | 4.0 |
| $H_3PO_4$ | 4.5 |
| $NaH_2PO_4$ | 3.5 |
| $KH_2PO_4$ | 4.4 |
| HCOOH | 4.5 |
| HOAc | 4.2 |
| Lactic Acid | 3.0 |
| Propionic Acid | 2.7 |
| Citric Acid | 3.5 |
| Ethylene diaminetetraacetic Acid | 2.8 |
| $CaHPO_4$ | 1.9 |
| Ascorbic Acid | 2.1 |

EXAMPLE 3

A cat litter was pelleted to a size of 5/32 inch diameter X ½ to ¾ inches long utilizing the following composition:

| | |
|---|---|
| Chopped and Ground Straw | 96.4% |

| | |
|---|---|
| Lignin Sulfonate | 2.5% |
| Tech. Grade Guar | 1.0% |
| PEL-AID "M" (a lubricant marked by Uniscope, Inc., Johnstown, Colorado) | 0.1% |

2400 grams of pellets were placed into a rectangular box 20 inches×–inches×5 inches. The depth of the pellets was 1.5 inches. The litter was used by an adult cat for 2 weeks before the odor of ammonia could be detected.

An identical composition was pelleted, with the addition of 10% sodium bisulfate and the same procedure was followed. The litter was used by an adult cat for 8 weeks before the odor of ammonia could be detected.

In comparison, a 100% alfalfa litter was pelleted, and the same test procedure was conducted. After 20 days an odor of ammonia could be detected from the litter.

We claim:

1. A method for controlling and eliminating ammonia odor from organic waste material comprising uniformly contacting said waste material with a composition consisting essentially of an effective amount of an ammonia control component selected from the group consisting of monobasic salts of dibasic acids, and mono-, di- or tribasic acids, selected from the group consisting of dithionic acid, sulfoxylic acid, formic acid, propionic acid, lactic acid, benzoic acid, ethylenediaminetetraacetic acid, maleic acid, citric acid, malonic acid, succinic acid, malic acid, adipic acid, and fumaric acid, wherein said ammonia control component has a dissociation constant, $pK_a$, less than the corresponding dissociation constant of aqueous ammonia.

2. The method of claim 1, wherein said waste material is selected from the group consisting of animal and human excreta.

3. The method of claim 1, wherein said ammonia control component is an alkali metal salt or an alkaline earth metal salt.

4. A method for controlling and eliminating ammonia odor from human or animal excreta comprising uniformly contacting said excreta with a composition consisting essentially of an effective amount of sodium bisulfate.

5. The method of claim 1, wherein said ammonia control composition is applied to the waste material in the form of a liquid, spray or pellet.

6. The method of claim 4, wherein said composition also contains a sufficient amount of an absorbent filler material.

7. The method of claim 6, wherein said filler is selected from the group consisting of straw, wood particles, ground peanut hulls, ground rice hulls, alfalfa, diatomaceous earth, calcium sulfate, and siliceous material.

8. The method of claim 4, wherein said ammonia control composition is utilized in the form of a pellet.

9. The method of claim 8, wherein said ammonia control composition includes lignin sulfonate.

10. The method of claim 9, wherein said pelleted composition includes natural or synthetic gums.

11. The method of claim 10, wherein said pelleted composition includes a pelleting additive.

12. An ammonia odor control composition consisting essentially of an effective amount of an ammonia control component selected from the group consisting of monobasic salts of dibasic acids, and mono-, di- or tribasic acids selected from the group consisting of dithionic acid, sulfoxylic acid, formic acid, propionic acid, lactic acid, benzoic acid, ethylenediaminetetraacetic acid, maleic acid, citric acid, malonic acid, succinic acid, malic acid, adipic acid, and fumaric acid, wherein said composition has a dissociation constant, $pK_a$, less than the corresponding dissociation constant of aqueous ammonia, and an absorbent filler material and wherein said composition is physically capable of being uniformly contacted with organic waste material to thereby eliminate and control odors of ammonia emanating therefrom.

13. The composition of claim 12, wherein said ammonia control component is an alkali metal salt or an alkaline earth metal salt.

14. The composition of claim 12, wherein said filler material is selected from the group consisting of straw, wood particles, ground peanut hulls, ground rice hulls, alfalfa, diatomaceous earth, calcium sulfate, and siliceous material.

15. The composition of claim 12, utilized in the form of a pellet.

16. The composition of claim 15, including lignin sulfonate.

17. The composition of claim 15, including a natural or synthetic gum material.

18. The composition of claim 15, including a pelleting additive.

19. An ammonia odor control composition for use on human or animal excreta, consisting essentially of an effective amount of sodium bisulfate as an ammonia control agent in combination with an absorbent filler material, and wherein said composition is physically capable of being uniformly contacted with human or animal excreta to thereby eliminate and control odors of ammonia emanating therefrom.

20. The composition of claim 19, wherein said filler material is selected from the group consisting of straw, wood particles, ground peanut hulls, ground rice hulls, alfalfa, diatomaceous earth, calcium sulfate, and siliceous material.

21. The composition of claim 19, in the form of a pellet, the amount of said sodium bisulfate being from 0.5 to 25% by weight.

22. The composition of claim 21, including lignin sulfonate.

23. The composition of claim 21, including a natural or synthetic gum material.

24. The composition of claim 21, including a pelleting additive.

* * * * *